United States Patent [19]

Davenport et al.

[11] 4,203,994
[45] May 20, 1980

[54] FUNGICIDAL 3-PHENYL-5-(SUBSTITUTED METHYL)ISOXAZOLES

[75] Inventors: James D. Davenport; Barry A. Dreikorn, both of Indianapolis, Ind.; A. Frederick Elsasser, Columbus, Ohio

[73] Assignee: Eli Lilly and Company, Indianapolis, Ind.

[21] Appl. No.: 904,687

[22] Filed: May 10, 1978

Related U.S. Application Data

[62] Division of Ser. No. 695,669, Jun. 14, 1976, Pat. No. 4,109,002.

[51] Int. Cl.$^2$ .................. A01N 9/22; A01N 9/28; A01N 9/00
[52] U.S. Cl. ...................................... 424/272; 424/249
[58] Field of Search .................... 424/272, 249

[56] References Cited

U.S. PATENT DOCUMENTS

| | | | |
|---|---|---|---|
| 2,946,720 | 7/1960 | Lewis | 424/272 |
| 3,629,474 | 12/1971 | Ghosh et al. | 424/272 |
| 3,769,295 | 10/1973 | Hoyle et al. | 260/307 F |
| 3,781,438 | 12/1973 | Gibbon | 424/272 |
| 3,869,466 | 3/1975 | Mixan | 260/302 S |

FOREIGN PATENT DOCUMENTS

| | | |
|---|---|---|
| 2215219 | 8/1974 | France . |
| 42-9146 | 5/1967 | Japan . |
| 44-29655 | 2/1969 | Japan . |
| 1164510 | 9/1969 | United Kingdom . |

OTHER PUBLICATIONS

J. Med. Chem. 9, 431–433 (1966), Sen et al.
J. Med. Chem. 10, 411–418 )167), Kano et al.

*Primary Examiner*—Douglas W. Robinson
*Attorney, Agent, or Firm*—Kathleen R. S. Page; Joseph A. Jones

[57] ABSTRACT

A class of isoxazoles having a phenyl or substituted-phenyl group at the 3-position and a substituted-methyl group at the 5-position are useful for the control of fungal foliar phytopathogens.

6 Claims, No Drawings

FUNGICIDAL 3-PHENYL-5-(SUBSTITUTED METHYL)ISOXAZOLES

This is a division of application Ser. No. 695,669, filed June 14, 1976, and issued Aug. 22, 1978, as U.S. Pat. No. 4,109,002.

BACKGROUND OF THE INVENTION

This invention relates to the field of agricultural chemistry and provides new plant protective fungicides.

The control of harmful microorganisms has long been a major concern of chemical research. In particular, the control of fungal foliar phytopathogens was one of the first goals of agricultural chemistry, and research in the field continues at a high pitch.

SUMMARY OF THE INVENTION

The present invention provides a new method of reducing the adverse effects of fungal foliar phytopathogens which comprises contacting the phytopathogens on the foliage of plants with an effective amount of a compound of the formula

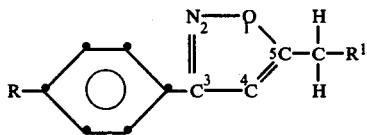

wherein
R represents
  chloro,
  bromo,
  fluoro,
  trifluoromethyl, or
  hydrogen;
$R^1$ represents
  bromo,
  chloro,
  isothiocyanato,
  amino,
  amino hydrochloride or hydrobromide,
  —NHCSNH($C_1$–$C_3$ alkyl),
  —NHCO$_2$($C_1$–$C_3$ alkyl), or
  3,5,7-triaza-1-azoniaadamantyl chloride or bromide.

In a preferred embodiment, the invention is particularly useful for the control of grape downy mildew. Fungicidal compositions are provided.

DESCRIPTION OF THE PREFERRED EMBODIMENT

In the above generic formula, the term $C_1$–$C_3$ alkyl refers to methyl, ethyl, propyl and isopropyl.

Particular classes of compounds which are contemplated as particularly efficacious in the method of this invention include the classes of compounds wherein:

1. R represents chloro, bromo, fluoro or trifluoromethyl;
2. R represents trifluoromethyl;
3. R represents chloro, bromo or fluoro;
4. R represents hydrogen;
5. $R^1$ represents isothiocyanato, amino, amino hydrochloride or hydrobromide, NHCSNH($C_1$–$C_3$ alkyl), NHCO$_2$($C_1$–$C_3$ alkyl) or 3,5,7-triaza-1-azoniaadamantyl chloride or bromide;
6. $R^1$ represents bromo or chloro;
7. $R^1$ represents NHCSNH($C_1$–$C_3$ alkyl) or NHCO$_2$($C_1$–$C_3$ alkyl);
8. $R^1$ represents bromo, chloro, isothiocyanato, amino, hydrochloride or hydrobromide, NHCSNH($C_1$–$C_3$ alkyl) or NHCO$_2$($C_1$–$C_3$ alkyl);
9. $R^1$ represents isothiocyanato, amino, amino hydrochloride or hydrobromide, NHCSNH($C_1$–$C_3$ alkyl) or NHCO$_2$($C_1$–$C_3$ alkyl);
10. $R^1$ represents isothiocyanato;
11. R and $R^1$ are as described by subparagraphs 1 and 5 above;
12. R and $R^1$ are as described by subparagraphs 1 and 6 above;
13. R and $R^1$ are as described by subparagraphs 1 and 7 above;
14. R and $R^1$ are as described by subparagraphs 1 and 8 above;
15. R and $R^1$ are as described by subparagraphs 1 and 9 above;
16. R and $R^1$ are as described by subparagraphs 1 and 10 above;
17. R and $R^1$ are as described by subparagraphs 2 and 5 above;
18. R and $R^1$ are as described by subparagraphs 2 and 6 above;
19. R and $R^1$ are as described by subparagraphs 2 and 7 above;
20. R and $R^1$ are as described by subparagraphs 2 and 8 above;
21. R and $R^1$ are as described by subparagraphs 2 and 9 above;
22. R and $R^1$ are as described by subparagraphs 2 and 10 above;
23. R and $R^1$ are as described by subparagraphs 3 and 5 above;
24. R and $R^1$ are as described by subparagraphs 3 and 6 above;
25. R and $R^1$ are as described by subparagraphs 3 and 7 above;
26. R and $R^1$ are as described by subparagraphs 3 and 8 above;
27. R and $R^1$ are as described by subparagraphs 3 and 9 above;
28. R and $R^1$ are as described by subparagraphs 3 and 10 above;
29. R and $R^1$ are as described by subparagraphs 4 and 5 above;
30. R and $R^1$ are as described by subparagraphs 4 and 6 above;
31. R and $R^1$ are as described by subparagraphs 4 and 7 above;
32. R and $R^1$ are as described by subparagraphs 4 and 8 above;
33. R and $R^1$ are as described by subparagraphs 4 and 9 above;
34. R and $R^1$ are as described by subparagraphs 4 and 10 above.

Throughout this document, all percentages, ratios and proportions are in weight units. All temperatures are on the Celsius scale.

The following typical compounds of this invention are mentioned to assure that agricultural chemists understand the invention. The compounds are exemplary of the invention but should not be interpreted as bounding the limits of it.

5-chloromethyl-3-(4-trifluoromethylphenyl)isoxazole
5-bromomethyl-3-(4-fluorophenyl)isoxazole 3-(4-fluorophenyl)-5-isothiocyanatomethylisoxazole
5-aminomethyl-3-(4-bromophenyl)isoxazole
5-aminomethyl-3-(4-chlorophenyl)isoxazole
5-aminomethyl-3-phenylisoxazole, hydrobromide
5-aminomethyl-3-phenylisoxazole
5-aminomethyl-3-(4-chlorophenyl)isoxazole, hydrochloride
1-methyl-3-[[3-(4-fluorophenyl)-5-isoxazolyl]methyl]-2-thiourea
1-ethyl-3-[[3-(4-chlorophenyl)-5-isoxazolyl]methyl]-2-thiourea
1-isopropyl-3-[[3-(4-bromophenyl)-5-isoxazolyl]methyl]-2-thiourea
1-propyl-3-[(3-phenyl-5-isoxazolyl)methyl]-2-thiourea
[[3-(4-trifluoromethylphenyl)-5-isoxazolyl]methyl]carbamic acid, methyl ester
[[3-(4-chlorophenyl)-5-isoxazolyl]methyl]carbamic acid, ethyl ester
[(3-phenyl-5-isoxazolyl)methyl]carbamic acid, isopropyl ester
[(3-phenyl-5-isoxazolyl)methyl]carbamic acid, propyl ester
1-[[3-(4-trifluoromethylphenyl)-5-isoxazolyl]methyl]-3,5,7-triaza-1-azoniaadamantane chloride
1-[[3-(4-bromophenyl)-5-isoxazolyl]methyl]-3,5,7-triaza-1-azoniaadamantane chloride
1-[[3-(4-fluorophenyl)-5-isoxazolyl]methyl]-3,5,7-triaza-1-azoniaadamantane bromide The preferred compounds of this invention are 5-bromomethyl-3-phenylisoxazole, 5-bromomethyl-3-(4-chlorophenyl)isoxazole, 5-aminomethyl-3-(4-chlorophenyl)isoxazole, 5-isothiocyanatomethyl-3-phenylisoxazole, and 1-methyl-3-[(3-phenyl-5-isoxazolyl)methyl]-2-thiourea.

The compounds of this invention are prepared by processes which are presently known to organic chemists, and which start from readily obtainable starting compounds. The preparation of all of the compounds begins with an appropriately substituted benzaldehyde, which is first reacted with hydroxylamine to form the corresponding aldehyde oxime. The hydroxylamine may be used in the form of a hydrohalide salt, in which case an acid scavenger, such as a tertiary amine, an alkali metal alkoxide, or an inorganic base such as sodium carbonate, sodium bicarbonate, potassium hydroxide and the like should be used in the reaction. The preferred solvent is an aqueous alkanol, but other solvents, such as diethyl ether, chloroform and the like are also satisfactory. The preferred reaction temperature is the reflux temperature of the reaction mixture.

The α-carbon of the aldehyde oxime is chlorinated, most easily by simple contact with free chlorine in chloroform. Low temperatures from about 0° to about 10° are preferred. The chlorinated oximes are the precursors of all the compounds of this invention. They are unstable in the pure form and are used without purification, although they may be isolated in the impure form.

The isoxazole ring of the compounds is formed by the reaction of the chlorinated oxime with a propargyl halide to form the isoxazole compound having the corresponding 3-phenyl substituent and a 5-halomethyl group. Such compounds are used in the invention, and are also used as intermediates for the preparation of other compounds. The ring closure step is performed at low temperatures in the range of 0° to 15° in the presence of a strong base, preferably triethylamine. The preferred reaction solvent is diethyl ether, although other typical inert reaction solvents may be used, such as tetrahydrofuran, benzene, alkanes and the like. Other bases besides triethylamine may be used, such as pyridine, sodium hydroxide, alkali metal alkoxides, lithium carbonate and the like.

A halomethyl compound is reacted with hexamethylenetetramine to form the triaza-1-azoniaadamantane compounds. The reaction is preferably carried out in chloroform at reflux temperature. Other solvents, such as diethyl ether, alkanes and benzene may be used at temperatures in the range of from 25° to 60°.

The aminomethyl salts are prepared by simple hydrolysis of the corresponding triazaadamantane compound with concentrated hydrochloric or hydrobromic acid at temperatures in the range of from room temperature to the reflux temperature, although reflux temperature is most convenient and preferred. An alkanol solvent is preferred. The salts may be neutralized with bases to prepare the free aminomethyl compounds.

The isothiocyanato compounds are readily prepared by reacting an aminomethyl compound with thiophosgene in the presence of a strong base, such as pyridine, triethylamine, sodium hydroxide, alkali metal alkoxide and the like. Reaction solvents such as chloroform, tetrahydrofuran and dimethylformamide at temperatures from about 0° to 10° are appropriate.

The thioureas are prepared by reacting an aminomethyl compound with an alkylisothiocyanate, as at reflux temperature in a solvent such as ethyl acetate, and the carbamic acid esters are prepared by reacting an aminomethyl compound with an alkylhaloformate, preferably at temperatures from about 0° to about 10° in the presence of a strong base as described above.

While the above general discussion, combined with the general knowledge of the art, is sufficient to enable an organic chemist to prepare any compound of this invention, the following specific preparative examples are supplied to assist the reader.

All of the compounds discussed below were identified by nuclear magnetic resonance analysis, infrared analysis, mass spectroscopy and elemental microanalysis procedures as was appropriate in each individual case.

The first examples below illustrate the closure of the isoxazole ring to form 5-halomethyl compounds.

EXAMPLE 1

5-bromomethyl-3-phenylisoxazole

A 121 g. portion of benzaldoxime was dissolved in 2 l. of chloroform and the solution was cooled to 5°. Dry gaseous chlorine was bubbled in, keeping the temperature of the mixture below 20°, until the solution turned first blue and then yellow. The solvent was then removed under vacuum at a temperature below 40°, and the residue was taken up in about 1.5 l. of diethyl ether and washed first with 500 ml. of 4 percent sodium hydroxide solution and then with 500 ml. of ice water. The organic solution was dried by filtering through sodium sulfate, and cooled below 5° C. A 120 g. portion of propargyl bromide was added and the mixture was stirred overnight and allowed to warm to room temperature. The reaction mixture was then treated with activated carbon and filtered. The filtrate was concentrated to about 400 ml., and the product was separated by the addition of petroleum ether. Two crops of crystals were obtained, giving a total of 117 g. of 5-bromomethyl-3-phenylisoxazole, m.p. 87°.

|   | Theoretical | Found |
|---|---|---|
| C | 50.45% | 50.71% |
| H | 3.39 | 3.51 |
| N | 5.88 | 5.91 |
| O | 6.72 | 6.93 |

EXAMPLE 2

5-bromomethyl-3-(4-chlorophenyl)isoxazole

The procedure of Example 1 was followed, starting with 156 g. of 4-chlorobenzaldoxime and 180 g. of propargyl bromide to produce 178 g. of product, m.p. 116°–117°.

|   | Theoretical | Found |
|---|---|---|
| C | 44.07% | 44.31% |
| H | 2.59 | 2.41 |
| N | 5.14 | 5.24 |
| O | 5.87 | 5.58 |

EXAMPLE 3

5-bromomethyl-3-(4-trifluoromethylphenyl)isoxazole

The same process was followed, starting with 51 g. of 4-trifluoromethylbenzaldoxime and 55 g. of propargyl bromide to produce 52 g. of product, m.p. 83°.

|   | Theoretical | Found |
|---|---|---|
| C | 43.17% | 43.22% |
| H | 2.31 | 2.32 |
| N | 4.58 | 4.81 |

The following two examples illustrate the preparation of the triaza-1-azoniaadamantyl compounds.

EXAMPLE 4

1-[(3-phenyl-5-isoxazolyl)methyl]-3,5,7-triaza-1-azoniaadamantane bromide

A 90 g. portion of the product of Example 1 was dissolved in 1.5 l. of chloroform and 70 g. of hexamethylenetetramine was added. The mixture was stirred at reflux temperature for 4 hours, and was filtered hot. The solids were dried under vacuum to obtain 143 g. of impure product, m.p. 159°–160°, which contained about 93 percent product and 7 percent hexamethylenetetramine.

EXAMPLE 5

1-[[3-(4-chlorophenyl)-5-isoxazolyl]methyl]-3,5,7-triaza-1-azoniaadamantane bromide The process above was followed, starting with 149 g. of the product of Example 2 and 100 g. of hexamethylenetetramine to produce 224 g. of the desired product, m.p. 188°–189°.

|   | Theoretical | Found |
|---|---|---|
| C | 46.79% | 46.99% |
| H | 4.17 | 4.57 |
| N | 17.05 | 17.31 |
| O | 3.90 | 3.64 |

Aminomethyl compounds are prepared as shown in the following series of examples.

EXAMPLE 6

5-aminomethyl-3-(4-chlorophenyl)isoxazole

A 205 g. portion of the product of Example 5 was dissolved in 1.5 l. of methanol and 250 ml. of concentrated hydrochloric acid was added. The mixture was stirred at reflux temperature overnight, and the solvent was then evaporated under vacuum. The residue was neutralized with aqueous sodium hydroxide and the product was extracted from the aqueous mixture with methylene dichloride and was purified by evaporating the solvent and recrystallizing the residue from ethanol-petroleum ether. The product was 78 g. of 5-aminomethyl-3-(4-chlorophenyl)isoxazole, m.p. 81°.

|   | Theoretical | Found |
|---|---|---|
| C | 57.57% | 57.35% |
| H | 4.35 | 4.35 |
| N | 13.43 | 13.65 |
| O | 7.67 | 7.47 |

EXAMPLE 7

5-aminomethyl-3-(4-trifluoromethylphenyl)isoxazole

The process of Examples 4 and 6 was followed, starting with 20 g. of the product of Example 3 and 30 g. of hexamethylenetetramine to prepare 22 g. of the corresponding triaza-1-azoniaadamantane compound, which was reacted with 50 ml. of hydrochloric acid in methanol and neutralized to obtain 8.8 g. of the desired product, m.p. 59°.

|   | Theoretical | Found |
|---|---|---|
| C | 54.55% | 54.63% |
| H | 3.75 | 3.45 |
| N | 11.57 | 11.49 |

EXAMPLE 8

5-aminomethyl-3-phenylisoxazole

A 10 g. portion of the product of Example 4 was reacted with hydrochloric acid as above to obtain 1.1 g. of the desired product, m.p. 50°.

|   | Theoretical | Found |
|---|---|---|
| C | 68.95% | 68.95% |
| H | 5.79 | 5.78 |
| N | 16.08 | 15.86 |
| O | 9.18 | 9.17 |

EXAMPLE 9

5-aminomethyl-3-phenylisoxazole, hydrochloride

A 2.4 g. portion of the product of Example 1 was reacted with 1.4 g. of hexamethylenetetramine in 25 ml. of ethanol in the presence of 2 g. of sodium iodide. The reaction mixture was stirred at reflux temperature until thin-layer chromatography indicated that the starting compound had all reacted. After the mixture was cooled, gaseous hydrogen chloride was bubbled in for 15 minutes, and the reaction mixture was dumped into a large amount of water. The aqueous mixture was washed with methylene dichloride, neutralized with 2 N sodium hydroxide, and extracted with additional methylene dichloride. The organic layer was evaporated to dryness under vacuum, and the residue was extracted with 1 N hydrochloric acid. The acid layer was washed with methylene dichloride and was then neutralized with sodium carbonate. The product was extracted from the neutral solution with chloroform. The solvent was evaporated under vacuum and the residue was recrystallized from hot chloroform and identified as 700 mg. of 5-amino-methyl-3-phenylisoxazole, hydrochloride, m.p. 222°.

|   | Theoretical | Found |
|---|---|---|
| C | 57.01% | 57.18% |
| H | 5.26 | 5.44 |
| N | 13.30 | 13.29 |
| O | 7.59 | 7.68 |

Synthesis of a typical isothiocyanato compound is illustrated by the following example.

EXAMPLE 10

5-isothiocyanatomethyl-3-phenylisoxazole

A 7 g. portion of the product of Example 8 was dissolved in 100 ml. of chloroform and cooled to ice bath temperature. Ten g. of thiophosgene in 15 ml. of chloroform and 23 g. of sodium carbonate in 150 ml. of water were added simultaneously. The mixture was stirred for 1 hour, and the organic layer was then separated. The water layer was extracted with chloroform, and the organic layers were combined, dried and evaporated to dryness under vacuum. The residue was taken up in diethyl ether and treated with activated carbon. After filtration, the ether solution was concentrated to about 75 ml. and about 250 ml. of petroleum ether was added, oiling out the product. Chromatography over a silica gel column purified the product, which was recrystallized from petroleum ether to produce 3.2 g. of 5-isothiocyanatomethyl-3-phenylisoxazole, m.p. 66°.

|   | Theoretical | Found |
|---|---|---|
| C | 61.04% | 60.79% |
| H | 3.73 | 3.56 |
| N | 12.95 | 12.84 |
| O | 7.40 | 7.45 |

EXAMPLE 11

3-(4-chlorophenyl)-5-isothiocyanatomethylisoxazole

A 7 g. sample of the product of Example 6 was reacted according to the scheme of Example 10 with 10 g. of thiophosgene to produce 2.4 g. of the desired product, m.p. 74°-76°.

|   | Theoretical | Found |
|---|---|---|
| C | 52.69% | 52.84% |
| H | 2.79 | 3.10 |
| N | 11.18 | 11.20 |
| Cl | 14.17 | 14.46 |

The examples immediately below illustrate the synthesis of thiourea compounds.

EXAMPLE 12

1-methyl-3-[(3-phenyl-5-isoxazolyl)methyl]-thiourea

A 7 g. portion of the product of Example 8 was dissolved in 200 ml. of ethyl acetate and 15 ml. of methyl isothiocyanate was added. The reaction mixture was stirred at reflux temperature for 3 hours, and was then evaporated to dryness under vacuum. The residue was taken up in ethyl acetate, treated with activated carbon and recrystallized by addition of petroleum ether. Further purification by chromatography over alumina gel was used, eluting impurities with chloroform and then eluting the product with 25 percent methanol-75 percent chloroform. The product-containing fractions were concentrated under vacuum, and the product was recrystallized from ethyl acetate-petroleum ether to produce 5 g. of 1-methyl-3-[(3-phenyl-5-isoxazolyl)methyl]-2-thiourea, m.p. 118°.

|   | Theoretical | Found |
|---|---|---|
| C | 58.28% | 58.20% |
| H | 5.30 | 5.32 |
| N | 16.99 | 17.12 |

EXAMPLE 13

1-methyl-3-[[3-(4-chlorophenyl)-5-isoxazolyl]methyl]-2-thiourea

The process above was repeated, starting with 8 g. of the product of Example 6 and 15 ml. of methylisothiocyanate to produce 4.6 g. of the desired product, m.p. 135°.

|   | Theoretical | Found |
|---|---|---|
| C | 51.15% | 51.45% |
| H | 4.29 | 4.08 |
| N | 14.91 | 15.17 |
| O | 5.68 | 5.70 |

The final two examples demonstrate the synthesis of carbamic acid esters of this invention.

EXAMPLE 14

[(3-phenyl-5-isoxazolyl)methyl]carbamic acid, ethyl ester

A 7 g. portion of the product of Example 8 was dissolved in 50 ml. of pyridine, cooled in an ice bath, and combined with 10 ml. of ethyl chloroformate. The mixture was stirred at ice bath temperature for 1 hour and allowed to warm to room temperature while being stirred for 2 hours more. The mixture was then poured into ice water and the crude product was separated by filtration and purified by chromatography over silica gel with ethyl acetate as the eluent. The yield was 6 g. of purified [(3-phenyl-5-isoxazolyl)-methyl]carbamic acid, ethyl ester, m.p. 82°.

|   | Theoretical | Found |
|---|---|---|
| C | 63.40% | 63.48% |
| H | 5.73 | 5.66 |
| N | 11.38 | 11.31 |
| O | 19.49 | 18.74 |

EXAMPLE 15

[[3-(4-chlorophenyl)-5-isoxazolyl]methyl]carbamic acid, ethyl ester

The process above was followed, starting with 8 g. of the product of Example 6 and 15 ml. of ethyl chloroformate to produce 3.7 g. of the desired product, m.p. 137°.

|   | Theoretical | Found |
|---|---|---|
| C | 55.62% | 55.81% |
| H | 4.67 | 4.40 |
| N | 9.98 | 10.03 |
| O | 17.10 | 16.92 |

The compounds of this invention have been tested to evaluate their ability to protect plants from the adverse effects of fungal foliar phytopathogens. The following examples illustrate the tests employed and the results produced by representative compounds.

In most of the tests, each compound was formulated for testing by dissolving or suspending about 3.5 weight percent of it in 50:50 acetone:ethanol containing about 10 g./100 ml of a nonionic surfactant. The solution was then dispersed in deionized water in a quantity such that the water dispersion contained the various compond concentrations indicated in the specific test methods and the table below. Concentrations are measured in parts per million, by weight (ppm).

In most of the tests, the compound dispersions were applied to the test plants by spraying them with an air atomizer, using sufficient dispersion to wet the plants thoroughly. Other methods of formulation and application were used in a few tests, as described in the specific test methods which follow.

Untreated, infected controls and untreated, normal controls were included in each test. The results are reported on a 1-5 rating scale where 1 indicates severe disease and 5 indicates complete control of the disease. An empty space in the table below shows that the indicated compound was not tested at the indicated rate. In some cases, more than one test was performed against a given phytopathogen, and the results in such cases are reported as averages. Compounds are identified by the example numbers used above.

Test 1 late blight of tomato

Four-week-old tomato seedlings were sprayed with aqueous dispersions containing test compounds at compound concentrations indicated in the table below. The following day, the foilage was inoculated with an aqueous suspension of propagules of *Phytophthora infestans*. The inoculum had been reared on infected wheat seed. The plants were held for two days in a moist chamber, and were then transferred to the greenhouse. The plants were observed and rated for disease control about one week after application of the test compounds.

Test 2 powdery mildew of beam

The host plants were 10-day-old bean seedlings. After aqueous dispersions containing test compounds at compound concentrations indicated in the table below had been sprayed on the foilage of the beans and allowed to dry, the plants were placed in the greenhouse and inoculated by storing them under other bean plants which were heavily infected with powdery mildew (*Erysiphe polygoni*). After about 10 days, the plants were observed and the results recorded as usual.

Test 3 anthracnose of cucumber

Aqueous dispersions containing test compounds at compound concentrations indicated in the table below were applied to healthy cucumber seedlings grown in sterilized greenhouse soil. The following day, the plants were inoculated with *Colletotrichum lagenarium* conidia as an aqueous suspension. The fungus had been grown on potato dextrose agar in petri dishes. The plants were held in a moist chamber for two days and transferred to the greenhouse, and the disease was observed and rated approximately 12 days after application of the test compounds.

Test 4 rice blast of rice

The test compound dispersions, at compound concentrations indicated in the table below, were applied to healthy rice seedlings growing thickly in plastic pots. The plants were inoculated on the next day with *Piricularia oryzae* (grown on rice polish agar) and the plants were held in a moist chamber for two days. The plants were then held in the greenhouse for 5–7 days and observed.

Test 5 helminthosporium leaf spot of wheat

Healthy wheat seed was planted in sterile greenhouse soil. When the seedlings were 4–5 inches tall, they were sprayed with test compound dispersions at compound concentrations indicated in the table below. The day after treatment, the plants were inoculated with a spore suspension of *Helminthosporium sativum* which had been grown on potato dextrose agar. The plants were placed in a moist growth chamber for two days to start disease growth, and were then transferred to the greenhouse. About a week after treatment, the plants were observed and the results were recorded.

Test 6 botrytis of grape

Sound grape berries were sterilized by immersion in diluted sodium hypochlorite and thoroughly rinsed. The berries were placed on wire screen shelves in compartmented Pyrex plates. The berries were then flamed and sprayed with test chemical dispersions. The following day, the berries were inoculated by spraying 5 ml. of a conidial suspension of *Botrytis cinerea* over each plate containing 12 berries. The inoculum had been grown on frozen lima bean agar. A small amount of water was added to each plate and a cover was sealed over each plate. After 48 hours at 25°, the berries were observed and disease ratings recorded.

Test 7 apple scab of apple

Apple seedlings at the 4–6 leaf stage were sprayed with aqueous dispersions of the test compounds. The following day, the plants were sprayed with a suspension of fresh conidia of *Venturia inaequalis* obtained from infected apple seedlings kept as a source of inoculum. The plants were held for two days in a 20° moist chamber to start disease growth and were then transferred to the greenhouse and observed 2-3 weeks later.

| Compound of Example No. | Appln. Rate ppm. | Late Blight | Powdery Mildew | Anthracnose | Rice Blast | Helminthosporium | Botrytis | Apple Scab | Downy Mildew | Cercospora |
|---|---|---|---|---|---|---|---|---|---|---|
| 1 | 400 | 3 | 1 | 2 | 2 | 1 | 1 | 5 | 5 | 1 |
|   | 100 |   |   |   |   |   |   | 4 | 3 |   |
|   | 80  | 1 |   | 1 | 1 |   |   |   |   |   |
|   | 25  |   |   |   |   |   |   | 4 | 1 |   |
|   | 6   |   |   |   |   |   |   | 1 |   |   |
| 2 | 400 | 1 | 4 | 1 | 2 | 1 | 1 | 1 | 5 | 2 |
|   | 100 |   | 1 |   |   |   |   |   |   | 1 |
|   | 25  |   | 1 |   |   |   |   |   |   | 1 |
| 3 | 400 |   | 1 | 1 | 1 | 1 | 1 |   | 5 | 1 |
| 4 | 400 | 1 | 1 | 2 | 1 | 1 | 1 | 1 |   | 1 |
| 5 | 400 | 1 | 1 | 2 | 1 | 1 | 1 | 1 | 1 | 1 |
|   | 100 |   |   | 1 |   |   |   |   |   |   |
|   | 25  |   |   | 1 |   |   |   |   |   |   |
| 6 | 400 | 1 | 1 | 4 | 1 |   |   |   | 4 | 3 |
| 7 | 400 | 1 | 1 | 1 | 1 |   |   |   | 5 | 1 |
| 8 | 400 | 1 | 1 | 1 | 2 | 1 | 1 | 1 |   | 1 |
| 9 | 400 | 1 | 1 | 1 | 1 | 1 | 1 | 4 | 1 | 1 |
|   | 100 |   |   |   |   |   |   | 1 |   |   |
|   | 25  |   |   |   |   |   |   | 1 |   |   |
| 10 | 400 | 1 | 1 | 1 | 2 | 1 | 1 | 4 |   | 1 |
|    | 100 |   |   |   |   |   |   | 4 |   |   |
|    | 25  |   |   |   |   |   |   | 4 |   |   |
|    | 6   |   |   |   |   |   |   | 1 |   |   |
| 12 | 400 | 1 | 1 | 2 | 3 | 1 | 1 | 1 | 3 | 3 |
|    | 100 |   |   | 1 | 3 |   |   |   |   |   |
|    | 25  |   |   | 1 | 1 |   |   |   |   |   |
| 14 | 400 | 1 | 1 | 1 | 1 | 1 | 3 | 1 | 1 | 4 |
|    | 100 |   |   |   |   |   |   |   |   | 1 |
|    | 25  |   |   |   |   |   |   |   |   | 1 | ferred to the greenhouse. About two weeks after application of the compounds, the plants were observed and the results were recorded.

Test 8 downy mildew of grape

Young expanding grape leaves were detached from healthy vines on the day of the test. Leaves were placed individually in plastic petri dishes, bottom side up, on top of an expanded plastic mat. Water was added to each petri dish, and the petiole of each leaf was wrapped with a water-soaked wad of cotton. Each leaf was sprayed with an aqueous dispersion of the compound to be tested.

After the test compound dispersions had dried, the leaves were inoculated by atomizing a conidial suspension of *Plasmopara viticola* (grown on infected leaf tissue) evenly over the leaf surface. The plates were then covered and were stored in a growth room at about 18° and 100% relative humidity where they were exposed to 8 hours a day of artificial light. After about a week of storage, all the leaves were observed and the signs of disease were evaluated.

Test 9 cercospora leaf spot of sugar beet

Sugar beet seedlings were transplanted into square plastic pots and allowed to grow for three weeks. Aqueous dispersions containing 400 ppm. of the compounds to be tested were sprayed on the leaf surfaces. After the dispersions dried, but within 24 hours, the plants were inoculated with a conidial suspension of *Cercospora beticola* which had been grown on sugar beet leaf decoction agar. After the plants were held in a moist Many of the compounds have been retested in replicated special tests against downy mildew and botrytis rot of grape. The test methods were the same as those described above, except that multiple replicates were used at the various rates. In many cases, the tests reported below have been repeated several times, and the results thereof have been averaged.

| Compound of Example No. | Appln. Rate ppm. | Downy Mildew | Botrytis |
|---|---|---|---|
| 1 | 800 | 5 | 1 |
|   | 400 | 5 | 1 |
|   | 200 | 4 | 1 |
|   | 100 | 3 |   |
|   | 50  | 2 |   |
|   | 25  | 2 |   |
| 2 | 800 | 4 | 1 |
|   | 400 | 5 | 1 |
|   | 200 | 5 | 1 |
| 4 | 800 | 5 | 1 |
|   | 400 | 4 | 1 |
|   | 200 | 2 | 1 |
| 5 | 800 | 4 |   |
|   | 400 | 5 |   |
|   | 200 | 3 |   |
| 6 | 800 | 4 | 1 |
|   | 400 | 4 | 1 |
|   | 200 | 4 | 1 |
| 7 | 800 | 3 | 1 |
|   | 400 | 4 | 1 |
|   | 200 | 1 | 1 |
| 8 | 800 | 1 | 1 |
|   | 400 | 3 | 1 |
|   | 200 | 3 | 1 |
|   | 100 | 3 | 1 |
| 9 | 800 | 4 | 1 |
|   | 400 | 3 | 1 |
|   | 200 | 2 | 1 |
| 10 | 800 |   | 5 |
|    | 400 | 5 | 4 |

-continued

| Compound of Example No. | Appln. Rate ppm. | Downy Mildew | Botrytis |
|---|---|---|---|
|  | 200 | 4 | 3 |
|  | 100 | 4 | 2 |
|  | 50 | 3 | 1 |
|  | 25 | 3 | 1 |
| 12 | 800 | 4 | 1 |
|  | 400 | 1 | 1 |
|  | 200 | 2 | 1 |
|  | 100 | 1 |  |
| 13 | 800 | 4 | 1 |
|  | 400 | 4 | 1 |
|  | 200 | 3 | 1 |
| 14 | 800 | 1 | 1 |
|  | 400 | 4 | 1 |
|  | 200 | 3 | 1 |
| 15 | 800 | 3 | 1 |
|  | 400 | 1 | 1 |
|  | 200 | 3 | 1 |

H. *Escherichia coli*
I. *Citrobacter freundii*
J. *Pseudomonas aeruginosa*
K. *Bordetella bronchiseptica*
L. *Salmonella typhimurium*
M. *Pseudomonas solanacearum*
N. *Erwinia amylovora*
O. *Candida tropicalis*
P. *Trichophyton mentagrophytes*
Q. *Aspergillus flavus*
R. *Ceratocystis ulmi*
S. *Pasteurella multocida* (bovine)
T. *Pasteurella multocida* (avian)
U. *Salmonella dublin*
V. *Pseudomonas sp.*
W. *Mycoplasma gallisepticum*
X. *Mycoplasma hyorhinis*
Y. *Mycoplasma hyopneumcniae*
Z. *Aeromonas liquefaciens*

| Cmp. of Ex. No. | A | B | C | D | E | F | G | H | I | J | K | L | M |
|---|---|---|---|---|---|---|---|---|---|---|---|---|---|
| 1 | 100 |  | 100 |  |  |  |  |  |  |  | 100 |  |  |
| 2 | <10 |  | 100 |  |  |  |  |  |  |  | <10 |  |  |
| 3 | <10 |  |  |  |  |  |  |  |  |  |  |  |  |
| 4 | 100 | 100 | 100 | 100 | 100 | 100 | 100 | 100 | 100 | 100 | 100 | 100 | 100 |
| 5 | 100 | 100 | 100 | 100 | 100 |  |  |  | 100 | 100 | 100 | 100 | 100 |
| 6 | 100 |  |  |  | 100 |  |  |  |  |  | 100 |  |  |
| 7 | 100 |  |  |  | 100 |  |  |  |  |  | 100 |  |  |
| 10 | <10 | 100 | 100 | 100 |  |  |  | 100 | 100 |  | 75 | 100 | 100 |
| 12 | 100 |  |  |  |  |  |  |  |  |  |  |  |  |
| 13 | <10 |  |  |  |  |  |  |  |  |  | 100 |  |  |
| 14 |  |  |  |  |  |  |  |  |  |  |  |  |  |

| Cmp. of Ex. No. | N | O | P | Q | R | S | T | U | V | W | X | Y | Z |
|---|---|---|---|---|---|---|---|---|---|---|---|---|---|
| 1 |  | 100 | <10 | 100 | <10 |  |  |  |  |  |  |  |  |
| 2 |  | <10 | <10 | <10 | <10 |  |  |  |  |  |  |  |  |
| 3 |  | 100 | 100 | 100 | 100 |  |  |  |  |  |  |  |  |
| 4 | 100 | 100 | 100 |  |  | 50 | 50 | 50 | 50 | 25 | 50 | 50 |  |
| 5 | 100 | 100 |  |  |  |  |  |  |  |  |  |  |  |
| 6 |  | 100 | 100 |  | 100 |  |  |  |  |  |  |  |  |
| 7 | 100 | 100 | 100 |  |  |  |  |  |  |  |  |  |  |
| 10 | 100 | <10 | <10 | 100 | <10 | 12 | 25 | 12 | 25 | 50 | 50 | 50 |  |
| 12 |  |  |  |  |  |  |  |  |  |  |  |  |  |
| 12 |  |  |  |  | 100 |  |  |  |  |  |  |  |  |
| 14 |  | 100 |  |  |  |  |  |  |  |  |  |  |  |

It is notable that the compounds of this invention can be used against other harmful pathogens, as well as against fungal foliar phytopathogens. For example, the following results were obtained when represenative compounds were tested in a system to determine their ability to inhibit the growth of microorganisms in vitro. The organisms named below were grown in culture media, appropriate for the growh of the various organisms, containing the compounds at various concentrations, measured in micrograms/milliliter. The table below lists the lowest concentration at which each compound inhibited the growth of the indicated microorganism.

A. *Staphylococcus aureus*
B. *Streptococcus faecalis*
C. *Proteus morganii*
D. *Salmonella typhosa*
E. *Klebsiella pneumoniae*
F. *Enterobacter aerogenes*
G. *Serratia marcescens*

Several of the compounds have also been found to be effective against aquatic weeds. For example, the compounds of Examples 1, 3 and 10 are effective against coontail, *Ceratophyllum demersum* L., hydrilla, *Hydrilla verticillata*, and duckweed, *Lemna minor* L., at concentrations of 10 ppm. or less.

The test data reported above show that the compounds of this invention are useful for the protection of plants from the adverse effects of a variety of fungal foliar phytopathogens. Accordingly, the invention is a new method of reducing the adverse effects of fungal foliar phytopathogens which comprises contacting the phytopathogens on the foliage of host plants with an effective phytopathogen-inhibiting amount of one of the compounds described above. The method is carried out by applying a compound of the invention to the plants to be protected.

A preferred aspect of the invention is its use to protect grape plants from downy mildew, which disease is caused by the phytopathogen *Plasmopara viticola*. The invention is used against downy mildew according to the general teachings below which describe use of the invention against phytopathogens in general.

Practice of the method does not necessarily kill the phytopathogens. As the data above show, application of a phytopathogen-inhibiting amount of a compound reduces the adverse effects of the disease, even though only a part of the phytopathogen population may be killed by the compound. The term "phytopathogen-inhibiting amount" is used here to describe an amount which is sufficient to reduce the adverse effects of a phytopathogen. The term "reducing the adverse effects" refers to weakening the pathogen sufficiently that its reproduction rate and its vigor are decreased, with the result that the express signs of the disease, and the concomitant injury to the host plant, are decreased as compared with phytopathogens growing on untreated plants.

As is usual in the plant protection art, best results are obtained by applying the compound several times during the growing season at intervals of from one to a few weeks, depending on the weather and the severity of the disease.

The methods of formulating the compounds and preparing dispersions of the formulations, and the methods of applying dispersions of the compounds to the plants to be protected, are entirely conventional in the plant protection art. Some explanation of the methods of application will be given merely to assure that those skilled in the art can carry out the invention without undue experimentation.

It is usual in describing foliar applications of plant protectants to measure the application rate by the concentration of the dispersion in which it is applied. The application rate is measured in this way because it is customary to apply a sufficient amount of the dispersion to cover the foliage with a thin film. The amount of dispersion applied is thus dependent on the foliar area of the plants being treated, and the quantity of plant protecting compound is dependent upon its concentration in the dispersion. In general, compound concentrations in the range of from about 50 to about 1500 parts of compound per million parts by weight of dispersion are used in the practice of this invention.

The compounds of this invention are usually applied in the form of fungicidal compositions which are important embodiments of the invention. Such compositions comprise a compound of this invention and a phytologically-acceptable inert carrier, and frequently are concentrated formulations which are dispersed in water for application, or are dust formulations. The compositions are prepared according to procedures and formulae which are conventional in the agricultural chemical art, but which are novel and important because of the presence therein of the compounds of this invention. Some description of the formulation of the fungicidal compositions will be given, to assure that agricultural chemists can readily prepare any desired fungicidal composition.

The dispersions in which the compounds are applied are most often aqueous suspensions or emulsions prepared from concentrated formulations of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usually from about 10 percent to about 90 percent by weight.

The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, expecially the high-boiling naphthalenic and olefinic portions of petroleum such as heavy aromatic naphtha. Other organic solvents may also be used, such as terpenic solvents including rosin derivatives, and complex alcohols such as 2-ethoxyethanol. Suitable emulsifiers for emulsifiable concentrates are chosen from the same types of surfactants used for wettable powders.

Adjuvants are frequently used to improve the ability of the aqueous dispersion to coat and adhere to foliage. Such adjuvants as gums, emulsified polybutenes, cationic surfactants and lignin derivatives can often increase the potency of the method in a specific use.

Less frequently, the compounds are applied to foliage in the form of dusts. Agricultural chemical dusts typically comprise the compound in a finely powdered form, dispersed in a powdered inert carrier. Most often, the carrier is a powdered clay, such as pyrophyllite, bentonite, a volcanic deposit, or montmorillonite. Dusts are usually prepared to contain concentrations of the compound at the highest part of the concentration range, such as 1500 ppm., and may contain even more active ingredient.

Dispersions of the compounds are applied in the usual manners. Low-pressure sprayers, high-pressure sprayers and low-volume air blast equipment are all effective for the application of water-dispersed compounds of the invention. Dust dispersions are readily applied by means of the usual equipment which blows the dust into intimate contact with the foliage.

We claim:

1. A fungicidal method of reducing the adverse effects of fungal foliar phytopathogens which comprises applying to the phytopathogens on the foliage of host plants an effective phytopathogen-inhibiting amount of a compound of the formula

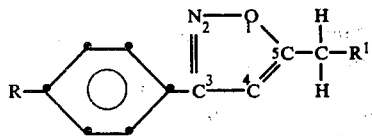

wherein
R represents
  chloro,
  bromo,
  fluoro,
  trifluoromethyl, or
  hydrogen;
$R^1$ represents
  bromo or chloro.

2. A method of claim 1 wherein the phytopathogen is *Plasmopara viticola* and the host plants are grapes.

3. A method of claim 1 wherein the amount of the compound is from about 50 to about 1,500 ppm.

4. A method of claim 2 wherein the amount of the compound is from about 50 to about 1,500 ppm.

5. The method of claim 1 wherein the compound is 5-bromomethyl-3-phenylisoxazole.

6. The method of claim 1 wherein the compound is 5-bromomethyl-3-(4-chlorophenyl)isoxazole.

* * * * *